United States Patent [19]

Dahm et al.

[11] 4,276,143

[45] Jun. 30, 1981

[54] APPARATUS FOR CONTINUOUSLY MEASURING ION CONCENTRATIONS

[75] Inventors: Franz-Ludwig Dahm, Alzenau; Herbert Diehl, Frankfurt; Kurt Eiermann, Pfungstadt; Reinhold Lamberty, Bornheim-Walberberg; Wolfgang Nischk, Wesseling, all of Fed. Rep. of Germany

[73] Assignee: Deutsche Gold und Silber Scheideanstalt vormals Roessler, Frankfurt, Fed. Rep. of Germany

[21] Appl. No.: 94,800

[22] Filed: Nov. 15, 1979

[30] Foreign Application Priority Data

Nov. 18, 1978 [DE] Fed. Rep. of Germany ....... 2850137

[51] Int. Cl.[3] .......................................... G01N 27/46
[52] U.S. Cl. ........................ 204/195 M; 204/195 R; 73/863.21; 73/863.81
[58] Field of Search ................. 204/195 R, 195 M; 73/421 R, 421 A, 422 TC

[56] References Cited

U.S. PATENT DOCUMENTS

| | | | |
|---|---|---|---|
| 2,585,811 | 2/1952 | Marks | 204/195 R |
| 2,851,655 | 9/1958 | Haddad | 204/195 R |
| 2,876,189 | 3/1959 | Spracklen et al. | 204/195 R |
| 2,884,366 | 4/1959 | Anderson et al. | 204/195 R |
| 3,011,336 | 12/1961 | Weiss | 73/421 R |
| 3,269,924 | 8/1966 | Nessler | 204/195 R |
| 3,504,549 | 4/1970 | Davis et al. | 73/422 TC |
| 3,789,670 | 2/1974 | Rosenwald | 73/421 R |
| 3,865,708 | 2/1975 | Light et al. | 204/195 M |
| 3,880,011 | 4/1975 | Johnson | 73/422 TC |
| 3,969,209 | 7/1976 | Mueller | 204/195 R |

Primary Examiner—T. Tung

[57] ABSTRACT

There is provided an apparatus for continuous measurement of ion concentration in solutions by means of ion sensitive electrodes, which apparatus consists of an electrode containing measuring cell and a dosaging device. This apparatus is particularly suited for measuring cyanide ion concentration in strong hydrochloride solution in the presence of cyanogen chloride. The dosaging device contains a degassing section and a reflecting plate to which the supply means for the working solution to be measured and for the necessary auxiliary reagents are directed, the supply means being in the form of screens or nozzles.

9 Claims, 1 Drawing Figure

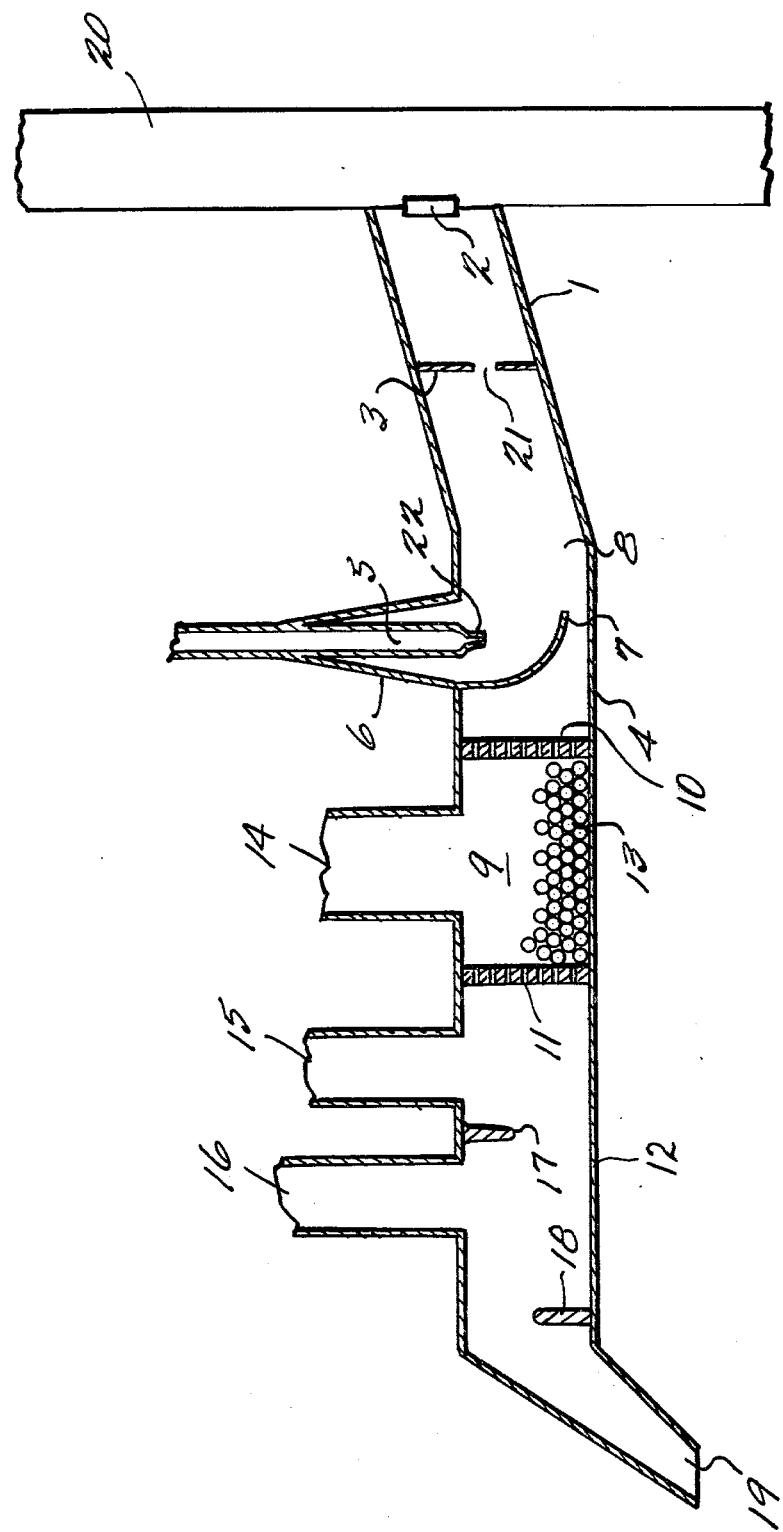

APPARATUS FOR CONTINUOUSLY MEASURING ION CONCENTRATIONS

BACKGROUND OF THE INVENTION

The invention is directed to an apparatus for the continuous measurement of ion concentrations by means of ion sensitive electrodes in solution, particularly for the measurement of cyanide ion concentration in strong hydrochloride solution in the presence of cyanogen chloride. The apparatus consists essentially of an electrode containing measuring cell, a dosaging device for the proper control of the solution to be measured and a connecting pipe for withdrawal of the solution being measured from the processing vessel.

It is known to determine ion concentrations in liquid media with the help of sensitive electrodes, which is particularly important for the control of continuous processes. Of particularly significance is a measuring method and a corresponding apparatus for the continuous measurement in corrosive media. Above all, is important the continuous determination of cyanide ion concentration in chemical syntheses, as well as e.g., continuous analysis of waste water.

These types of apparatus are known in the practice (e.g. K. Cammann; das Arbeiten mit ionenselektiven Elektroden Springer-Verlag, 1967, pages 190-194; F. Oehme, CZ-Chemie-Technik, 1974, pages 27-34). Such apparatus generally consist of a measuring cell which contains essentially the sensitive electrodes, and a dosaging device in which the solution to be measured is treated with conditioning solutions for the proper control of the solution to be measured. The conditioning solutions normally contain reagents for establishing a specific pH, sequestering agents for masking disturbing ions and other auxiliary reagents. These solutions are sucked in via electrical pumps, preferably tubular pumps, mixed, in a given case by means of a stirrer, and fed to the measuring cell.

The known apparatus, however, have the disadvantage that they are very prone to problems with strongly corrosive and gas forming liquids, particularly by using moving parts, such as pumps, stirrers or magnetic valves.

However with corrosive media the question of material plays a decisive role. Metals and flexible synthetic resin materials, as they are used, e.g. for hose connections, frequently lead to failures of the apparatus in question. These can have serious consequences for the entire process since the subsequently connected control devices with the failures of the measuring apparatus receive false information.

Furthermore the down time of these apparatuses with mechanically moving parts is relatively long and leads to a very sluggish control behavior.

Therefore it was the problem of the present invention to provide an apparatus for the continuous measurements of ion concentrations by means of ion sensitive electrodes in solutions, particularly for the measurement of cyanide ion concentrations in strong hydrochloride solutions in the presence of cyanogen chloride, which consists essentially of an electrode containing measuring cell, a dosaging device for the proper control of the solution to be measured and a connecting pipe for withdrawal of the solution to be measured from the processing vessel, which has to the least extent possible moving parts and whose down time is as short as possible.

SUMMARY OF THE INVENTION

This problem was solved according to the invention by making the dosaging apparatus tubular and containing a reflecting plate and a degassing section using packing and by building the supply means for the working solution to be measured and the supply means for the necessary auxiliary agents for the proper control for the dosaging device in the form of nozzles and/or screens.

BRIEF DESCRIPTION OF THE DRAWINGS

The single FIGURE of the drawings is a schematic illustration of the apparatus of the invention.

The apparatus can consist essentially of or consist of the stated parts. Unless otherwise indicated all parts and percentages are by weight.

DESCRIPTION OF THE PREFERRED EMBODIMENTS

Referring more specifically to the drawings the apparatus consists essentially of a connecting pipe 1, the dosaging device 4 and the electrode containing measuring cell 12.

The working solution whose ion concentration is to be measured goes via the connecting pipe 1 having the fused glass frit 2 in the circulating line 20 of a reaction vessel to the replaceable dosaging screen 3 and into the dosaging device 4, which preferably consists of glass. The necessary auxiliary reagents for proper control of the working solution are supplied at will in each case with a dosaging nozzle 5 which itself is located in a fused connecting piece 6 on the dosaging device. A deflecting plate 7 is so arranged in the meeting point of the different liquid jets that the working solution is measured, only after being rendered turbulent in the mixing chamber 8, on arrival at the electrode containing measuring cell 12 via the degassing section 9 which is bounded by perforated discs 10 and 11. In the degassing section 9 there is located packing 13 which causes a degassification and a further mixing of the material to be measured and besides provides for the smallest possible dead volumes. The gases which are liberated are removed via the connecting line 14 in which a temperature measuring instrument can also be arranged.

The electrode containing measuring cell 12 consists of two short tubes 15 and 16 which are provided for reception of the electrodes. The dam 17 causes a uniform flow of the working solution at the electrode. An overflow dam 18 which maintain the liquid level of the measuring apparatus is advantageously employed. The working solution leaves the apparatus via the outlet 19.

The nozzle 5 and/or the screens 3 for reasons of corrosion advantageously consist of synthetic corundum, especially of sapphire. The nozzle 22 or screen openings 21 preferably are so dimensioned that the outlet velocity of the solutions supplied to the dosaging device is in the range of 1-15 meters/sec.

The apparatus of the invention will be further explained with the help of a specific example. The apparatus set forth in the drawings serves for the continuous measurement of the cyanide ion concentration in the cyanogen chloride synthesis. A 14.6% hydrochloric acid solution is supplied via the glass frit 2 and the screen 3. The solution contained 5% cyanogen chloride, 0.3% hydrocyanic acid and 0.25% of ammonium chloride. From the supply pressure of 0.4 bar of the working solution at the screen 3 and the diameter of 0.2 mm of the screen opening 21 there results a dosaged volume of 1000 milliliters/h. As material for the dosaging screen there is employed sapphire which is made impervious with the help of a polytetrafluoroethylene band. As auxiliary reagents there is dosaged in via the nozzle shaped supply 5 a 23% aqueous sodium hydroxide for the adjustment of the pH required for the measurement. From the supply pressure and likewise the 0.2 mm diameter of the nozzle openings 22 there results a dosaged volume of 2000 milliliters/h. As packing 13, which advantageously should be voluminous and should have a large surface area, there were used glass balls (2 mm). Besides the flow through 1.8 mm holes in the perforated discs (10 and 11) there are located in the upper half in each an about 4 mm² opening which should prevent liquid stagnation. In the connecting line 14 there is a resistance thermometer which serves for the automatic temperature compensation of the measured value. Besides the gas set free is drawn off via this connecting line. The measuring elements consists of a cyanide-ion sensitive electrode in short tube 15 and a reference electrode arranged in the short tube 16. The liquid level of the apparatus is fixed through the about 6 mm high overflow dam 18.

For this case of use there is used as working material laboratory glassware for the entire apparatus.

Advantageously, there is used for the connecting pipe 1 a tube having a narrow bore in order to hold the downtime volume as small as possible.

The apparatus of the invention has no moving parts and a very small downtime so that there is little susceptible to disturbance and there is produced a very quick regulating behavior.

The screens 3 can also be build as nozzles or the nozzles 5 can be built as screens.

Applicants hereby incorporated by reference the entire disclosure of the German priority applicant No. P 28 50 137.3.

What is claimed is:

1. Apparatus for the continuous measurement of ion concentrations in solution by ion sensitive electrodes, particularly for the measurement of cyanide ion concentrations in strong hydrochloride solutions in the presence of cyanogen chloride, comprising in series:
   means for supplying solution to be measured to said apparatus;
   a dosage device connected to said supplying means for dosing the solution with a dosing liquid, said device including a mixing chamber, an inlet to said chamber for dosing liquid including restriction means for forming at least one jet of the dosing liquid directed into said chamber, deflector means in the path of the jet, and an inlet to said chamber for the solution including restriction means for forming at least one jet of the solution directed into said chamber toward and at an angle to the liquid dosing jet;
   a degassing section connected to said dosage device and having an outlet for gas; and
   a measuring cell containing ion-sensitive electrodes connected to said degassing section.

2. An apparatus according to claim 1 wherein said supply means is made of corundum.

3. An apparatus according to claim 1 wherein the dosage inlets are so dimensioned that the exit velocity of the dosed solution from the device is in the range of 1 to 15 meters/sec.

4. An apparatus according to claim 3 wherein the measuring cell has a discharge section provided with an overflow dam.

5. An apparatus according to claim 1 wherein the measuring cell has a discharge section provided with an overflow dam.

6. An apparatus according to claim 5 wherein the packing is voluminous and has a large surface area.

7. An apparatus according to claim 1 wherein the packing is voluminous and has a large surface area.

8. An apparatus according to claim 5 wherein the supply means for the solution to be measured comprises a connecting piece communicating with a processing vessel through a fused frit.

9. An apparatus according to claim 1 wherein the supply means for the solution to be measured comprises a connecting piece communicating with a processing vessel through a fused frit.

* * * * *